United States Patent [19]

Krebs et al.

[11] Patent Number: 4,910,319
[45] Date of Patent: Mar. 20, 1990

[54] PROCESS FOR PREPARING 3-AMINO-1-BENZYLPYRROLIDINES

[75] Inventors: Andreas Krebs, Odenthal; Thomas Schenke, Bergisch-Gladbach, both of Fed. Rep. of Germany

[73] Assignee: Bayer Aktiengesellschaft, Leverkusen, Fed. Rep. of Germany

[21] Appl. No.: 250,294

[22] Filed: Sep. 28, 1988

[30] Foreign Application Priority Data

Oct. 2, 1987 [DE] Fed. Rep. of Germany ....... 3733289

[51] Int. Cl.⁴ ............................................ C07D 207/14
[52] U.S. Cl. .................................... 548/557; 548/546
[58] Field of Search .......................................... 558/557

[56] References Cited

U.S. PATENT DOCUMENTS 3,433,801  3/1969  Dawson ............................. 548/557
3,433,802  3/1969  Dawson et al. ..................... 548/557

FOREIGN PATENT DOCUMENTS 267513   1/1969  Austria .
0028161  3/1978  Japan ................................. 548/557
0022699  2/1980  Japan ................................. 548/557

OTHER PUBLICATIONS

Farcasiu et al.; Revue Roumaine de Chimie, 15, 253–258 (1970).
Uskokovic et al.; The Journal of Organic Chemistry, vol. 27 (1962), pp. 3606–3608.
Cignarella et al.; The Journal of Organic Chemistry, vol. 26 (1961), pp. 2747–2750.
Mehta et al.; The Journal of Organic Chemistry, vol. 25 (1960), pp. 1012–1015.
Advanced Organic Chemistry, Reactions, 3rd Edition, Jerry Marrch, 1985, pp. 689–691.
Practical Catalytic Hydrogenation, Techniques and Applications, 1971, pp. 414–417, Freifelder.
Practical Catalytic Hydrogenation, Techniques and Applications, 1971, pp. 39–47, Freifelder.
Journal of Medicinal Chemistry, vol. 10 (Dec. 1967), pp. 1015–1021; Welstead et al.
Journal of Medicinal Chemistry, vol. 11 (1968), pp. 1034–1037; Helsley et al.
Journal of Medicinal Chemistry, vol. 20, No. 6 (Jan. 1977), pp. 801–805; Witiak et al.

Primary Examiner—Joseph Paul Brust
Attorney, Agent, or Firm—Sprung Horn Kramer & Woods

[57] ABSTRACT

A process for preparing a 3-amino-1-benzyl-pyrrolidine of the formula

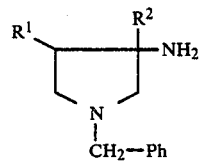

(I)

in which
$R^1$ and $R^2$ each independently is H or alkyl, and
Ph is phenyl, comprising reacting a 1-benzyl-$\Delta^3$-pyrroline-2,5-dione of the formula

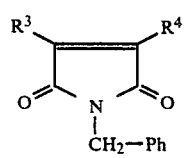

(II)

in which
$R^3$ and $R^4$ each independently is H or alkyl, with a nitrogen nucleophile of the formula $R^5NH_2$  (III)

in which
$R^5$ is H, benzyl, naphthylmethyl or phenyl-$CHR^6$, and
$R^6$ is $C_1$-$C_6$-alkyl or phenyl, to give an optionally substituted 3-amino-1-benzylpyrrolidine-2,5-dione of the formula

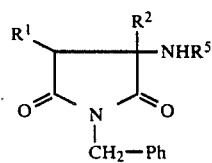

(IV)

and, if $R^5 \ne H$, the protecting group $R^5$ is subsequently cleaved off to give a 3-amino-1-benzylpyrrolidine-2,5-dione of the formula

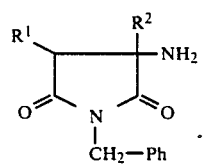

(IVa)

and completely reducing the carbonyl groups to form the 3-amino-1-benzylpyrrolidine of the formula (I).

11 Claims, No Drawings

PROCESS FOR PREPARING 3-AMINO-1-BENZYLPYRROLIDINES

The present invention relates to a new process for preparing partly known 3-amino-1-benzylpyrrolidines which can be substituted at the 3- and/or 4-position and also at the amine radical.

It is already known that 3-arylaminopyrrolidines can be obtained by the hydrogenolytical debenzylation of the corresponding 3-arylamino-1-benzylpyrrolidines. These pyrrolidines are obtained by reaction of anilines either with 1-benzyl-3-chloro- or with 1-benzyl-3-tosyloxypyrrolidines (J. Med. Chem. 10, 1015 (1967)).

1-Benzyl-3-(N-ethyl-N-methylamino)-pyrrolidine can be obtained by a lithium aluminum hydride reduction of 3-acetylamino-1-benzylpyrrolidine-2,5-dione, followed by methylation with formaldehyde (J. Med. Chem. 20, 801 (1977)).

3-Amino-1-benzylpyrrolidine has been obtained by hydrogenation of 1-benzyl-3-hydroximinopyrrolidine (Japan. Kokai 7828161). 3-Amino-1-benzylpyrrolidine has also been obtained by reaction of 1-benzyl-3-phthalimidopyrrolidine with hydrazine (J. Med. Chem. 11, 1034 (1968)). Both processes for preparing 3-amino-1-benzylpyrrolidine have in common that the required starting materials must be prepared in a many-step synthesis involving heavy losses of material (see, for example, U.S. Pat. No. 3,691,197, J. Org. Chem. 30, 740 (1965)).

Furthermore, it is known that N-phenylmaleimide can be reacted with methylamine to give 3-methylamino-1-phenylpyrrolidine-2,5-dione which can be reduced with lithium aluminum hydride to give 3-methylamino-1-phenylpyrrolidine (J. Med. Chem. 10, 1015 (1967)).

3-Dimethylaminopyrrolidine has been obtained by addition of dimethylamine to N-benzylmaleimide to give 1-benzyl-3-dimethylaminopyrrolidine-2,5-dione followed by lithium aluminum hydride reduction and catalytic hydrogenation (Eur. J. Med. Chem. 13, 479 (1978)).

3-Aminopyrrolidines having identical substituents on both nitrogen atoms are obtained in the reaction of 1,2,4-trisubstituted butanes with amines (EP 0,218,249).

Nothing is known about the addition of nitrogen nucleophiles to 1-benzyl-Δ³-pyrroline-2,5-diones for preparing 3-amino-1-benzylpyrrolidines.

It has now been found that 3-amino-1-benzylpyrrolidines of the formula (I)

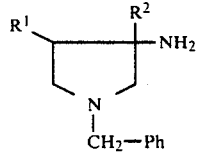

in which $R^1$ and $R^2$, which may be identical or different, each denote H or alkyl, preferably H or $C_1$–$C_6$-alkyl, but denote in particular H, are obtained by reacting 1-benzyl-Δ³-pyrroline-2,5-diones of the formula (II) with nitrogen nucleophiles of the formula (III) to give optionally substituted 3-amino-1-benzylpyrrolidine-2,5-diones of the formula (IV)

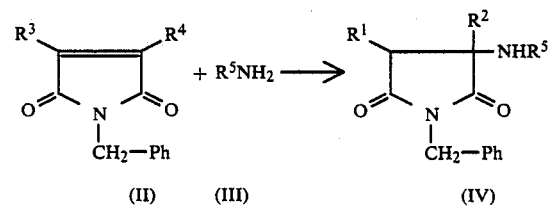

in which $R^3$ and $R^4$, which may be identical or different, each denote H or alkyl, preferably H or $C_1$–$C_6$-alkyl, but denote in particular H, $R^5$ either denotes H, benzyl, naphthylmethyl or a substituent Ph-CHR$^6$ where $R^6$ is $C_1$–$C_6$-alkyl or phenyl and $R^1$ and $R^2$ have the abovementioned meaning, and, in the case where $R^5$ is not H, subsequently cleaving off the protecting group $R^5$ to give 3-amino-1-benzylpyrrolidine-2,5-diones (IVa)

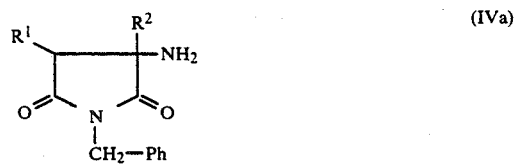

in which $R^1$ and $R^2$ have the abovementioned meaning, and, by complete reduction of the carbonyl groups, converting (IVa) to 3-amino-1-benzylpyrrolidines (I)

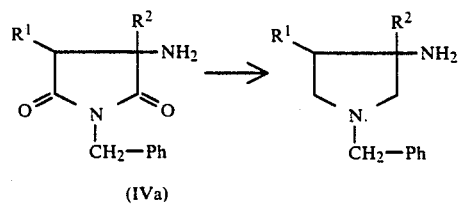

in which $R^1$ and $R^2$ have the abovementioned meaning.

In addition, it has been found that 3-aralkylamino-1-benzylpyrrolidines of the formula (V) are obtained by reducing the 3-aralkylamino-1-benzylpyrrolidine-2,5-diones of the formula (IVb)

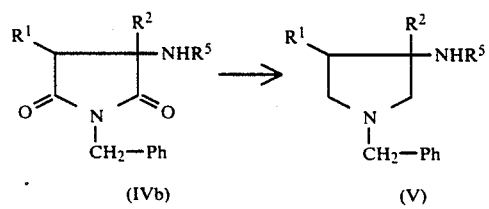

in which $R^1$, $R^2$ and $R^5$ have the abovementioned meaning, but $R^5$ is not H.

The first reaction step of the process according to the invention, the addition of nitrogen nucleophiles of the formula (III) to 1-benzyl-Δ³-pyrroline-2,5-diones of the formula (II) is carried out by reacting the reactants together in a solvent or even in the absence of a solvent at temperatures from −40° C. to +200° C. The choice of solvent and reaction temperature is dependent on the reactivity of the starting materials and on their tendency to enter into side reactions or secondary reactions with the product.

The solvents which can be used in pure form or as a mixture are: aliphatic and aromatic hydrocarbons such as, for example, ligroin, cyclohexane, toluene, xylene and tetralin, open-chain and cyclic ethers such as, for example, diethyl ether, methyl tert.-butyl ether, di-n-butyl ether, dimethoxyethane, diethylene glycol dimethyl ether, diethylene glycol diethyl ether, tetrahydrofuran, dioxane and anisole, chlorinated hydrocarbons such as chlorobenzene, chloroform and 1,2-dichloroethane, esters such as ethyl formate, ethyl acetate, glycol monomethyl ether acetate and n-butyl acetate and also dipolar aprotic solvents such as dimethylformamide, dimethyl sulphoxide, N-methylpyrrolidinone, N-methylcaprolactam, tetramethylurea and sulpholane.

Preference is given to aromatic hydrocarbons and to cyclic and open-chain ethers and mixtures thereof.

In the case of $R^5 \neq H$, it is appropriate to react the reactants with each other in a stoichiometric or approximately stoichiometric ratio, whereas in the case of $R^5 = H$ even an excess of ammonia may be desirable.

The reaction can either be carried out such that the nitrogen nucleophile of the formula (III) is added to 1-benzyl-$\Delta^3$-pyrroline-2,5-dione of the formula (II), it being possible for both reaction participants to be present as solids or in solution, or such that the compounds of the formula (II) are added to an initially introduced compound of the formula (III). However, it is also possible to meter both reaction participants simultaneously into a reaction vessel. The reaction can be carried out at atmospheric pressure, reduced pressure and even at elevated pressure.

The way in which the reaction is carried out is dependent inter alia on the reactivity of the nitrogen nucleophile (III), in particular, if ammonia is used ($R^5 \neq H$) it is reasonable to introduce excess ammonia to reduce secondary reactions of the products of the type (IVa) with starting materials of the formula (II) in the form of a further addition.

The substituted 3-amino-1-benzylpyrrolidine-2,5-diones of the formula (IV) obtained are partly known, but they were until now prepared by a different method (see, for example, J. Am. Chem. Soc. 70, 3778 (1948), J. Pharm. Sci. 70, 192 (1981)).

To prepare the 3-amino-1-benzylpyrrolidine-2,5-diones (IVa), it is necessary, if ammonia was not used as the nitrogen nucleophile of the formula (III) ($R^5 = H$) in the addition reaction, to cleave off the protecting group from the 3-amino substituent of the pyrrolidine-2,5-diones (IV).

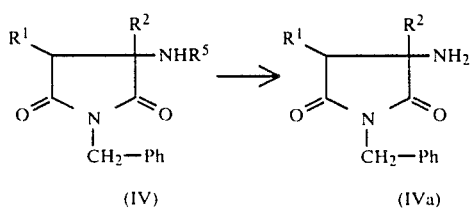

The elimination of the protecting group is achieved by catalytic hydrogenation. Solvents which can be used are alcohols, cyclic and open-chain ethers, carboxylic acids, alcoholic hydrochloric acid, alkylaromatics and mixtures thereof or mixtures with water. The catalysts used as palladium, palladium on supports such as, for example, active charcoal, platinum, Raney nickel or Raney cobalt at temperatures from 0° to 200° C. and hydrogen pressures from 1 to 300 bar. Alcohols or ethers are preferably used as solvents and palladium on charcoal as the catalyst.

The reduction of the carbonyl groups of (IVa) to give 3-amino-1-benzylpyrrolidines (I) and of 3-aralkylamino-1-benzylpyrrolidine-2,5-diones of the formula (IVb) to give 3-aralkylamino-1-benzylpyrrolidines of the formula (V) can be achieved by catalytic hydrogenation or by reaction with hydrides or complex hydrides of elements of the 3rd main group. The hydride which is preferably used is boron hydride, including the form of complexes with Lewis acids or Lewis bases, and the complex hydrides which are preferably used are sodium bis-(2-methoxyethoxy) aluminum hydride, lithium aluminum hydride and also sodium borohydride, with or without additional Lewis acids such as, for example, titanium tetrachloride, tin tetrachloride, aluminum trichloride, boron trifluoride, iron trichloride and antimony pentachloride.

The reductions are carried out in inert organic solvents such as cyclic or open-chain ethers such as, for example, diethyl ether, methyl tert.-butyl ether, di-n-butyl ether, dimethoxyethane, diethylene glycol dimethyl ether, diethylene glycol diethyl ether, tetrahydrofuran or dioxane or alkylaromatics such as, for example, toluene, xylene and tetralin or mixtures thereof at temperatures from 0° to 200° C. To obtain higher reaction temperatures and shorter reaction times, the reduction with hydrides or complex hydrides can also be carried out at pressures >1 bar.

In a special embodiment of the process, the individual intermediates are not isolated but are in each case used as a reaction solution in the next step. No or only small chemical losses in yield are caused by this simplification, and the losses due to work up are limited to the last reaction step. In this case, the solvents which can be used are those which are suitable for all reaction steps such as cyclic and open-chain ethers and alkylaromatics.

It is particularly surprising that 3-amino-1-benzylpyrrolidines of the formula (I) can be prepared in such good yields by the process according to the invention. In particular, it could not be expected that the reaction sequence without isolating the intermediates can be carried out with such high yields. In view of the prior art, it had to be expected that side reactions and secondary reactions would lead to losses in the yields and would be accompanied by contamination of the intermediates which would require their isolation.

Thus, for example in the case of the addition of benzylamine to 1-benzyl-$\Delta^3$-pyrroline-2,5-dione, it should be expected that the ring opening as a side reaction or secondary reaction would lead to losses in the yield and to contamination of the product, since it is known that in the addition of primary amines to 1-benzyl-$\Delta^3$-pyrroline-2,5-dione a double addition with ring opening to give amino succinic diamides can occur even at room temperature (Revue Roumaine de Chimie 15, 253 (1970)).

Furthermore, in the case of the addition of the nitrogen nucleophiles of the formula (III) onto 1-benzyl-$\Delta^3$-pyrroline-2,5-diones of the formula (II), it was to be expected that the addition product of the formula (IV) enters into another addition reaction with the starting compound of the formula (II) (cf. J. March, Advanced Organic Chemistry, page 689, 3rd edition, John Wiley & Sons, New York 1985).

In the case of the elimination of the protecting group $R^5$ of the formula (IV) to give 3-amino-1-benzylpyrrolidine-2,5-diones (IVa), difficulties were to be expected, in particular, if the reaction solution was intended to be used immediately in the next reaction step. Thus, for example, in the debenzylation of 1-benzyl-3-benzylaminopyrrolidine-2,5-dione to give 3-amino-1-benzylpyrrolidine-2,5-dione, a simultaneous elimination of the 1-benzyl group could not be ruled out, since sometimes the N-benzyl groups in amides are cleaved off by hydrogenolysis under relatively mild conditions (J. Org. Chem. 27, 3606 (1962)). Furthermore, even in the case of the elimination of a carbobenzoxy protecting group—which always occurs more easily than the hydrogenolysis of an N-benzyl radical—a competing ring opening has been observed with 3-benzyl-8-carbobenzoxy-3,8-diazabicyclo [3.2.1]-2,4-dione (J. Org. Chem. 26, 2747 (1961)). It was to be expected that these side reactions would lead to difficulties especially in the case where, due to the limited selection of solvents in a reaction sequence without isolation of the intermediates, particularly drastic reaction conditions would have to be used in the catalytic debenzylation.

The reason for this is that the hydrogenolytic cleavage of benzylamines is frequently carried out in protic solvents in the presence of an acid to prevent the poisoning of the catalysts by free amides (M. Freifelder, "Practical Catalytic Hydrogenation", p. 39 and p. 414, Wiley-Interscience New York 1971).

The process according to the invention has a number of advantages. It uses 1-benzyl-$\Delta^3$-pyrroline-2,5-diones, which can be obtained, for example, in a simple manner from maleic anhydride or citraconic anhydride and benzylamine, as the starting materials (J. Org. Chem. 25, 1012–1015 (1960). The reaction steps of the process according to the invention give very good yields in most cases. Furthermore, it is often possible, without having to accept drawbacks, to carry out several reaction steps in the same solvent without work up of the intermediates.

If 1-benzyl-$\Delta^3$-pyrroline-2,5-dione is used as the starting material, benzylamine as the nitrogen nucleophile, lithium aluminum hydride as the reducing agent and palladium on charcoal for the debenzylation, the reaction sequence can be represented by the following formula scheme:

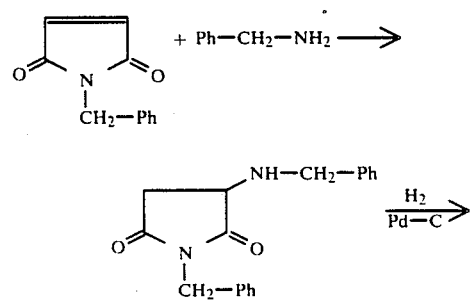

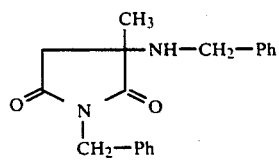

The compounds of the formula (I) are used as intermediates for preparing 3-aminopyrrolidine or 3-tert.-butyloxycarbonylaminopyrrolidine, which are needed for the synthesis of antibacterial quinolonecarboxylic acid derivatives (cf. EP 153,163, EP 218,249, DE 3,601,517 and U.S. Pat. No. 4,382,937).

EXAMPLES

Example 1

1-Benzyl-3-benzylaminopyrrolidine-2,5-dione

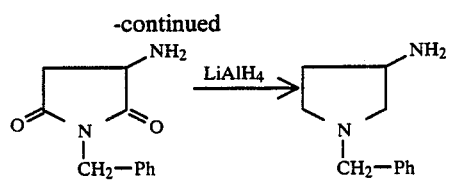

37.4 g (0.2 mol) of 1-benzyl-$\Delta^3$-pyrroline-2,5-dione is initially introduced in 100 ml of tetrahydrofuran, and at 20° C. 21.4 g (0.2 mol) of benzylamine are added dropwise to this mixture causing the temperature to rise to 40° C. Stirring is continued for another hour at that temperature, and the solvent is then removed at 6 mbar in a rotary evaporator having a bath temperature of up to 80° C. This gives a residue of 59.3 g of a solid having a product content of 96%, determined by gas chromatography. The yield is 97% of theory, and the melting point 60° to 63° C.

Example 2

1-Benzyl-3-benzylamino-3-methylpyrrolidine-2,5-dione

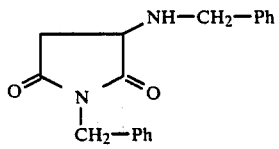

120.6 g (0.6 mol) of N-benzylcitraconimide and 65.2 g (0.6 mol) of benzylamine are heated to reflux in 600 ml of tetrahydrofuran for 16 hours. The solvent is then distilled off, and the residue is chromatographed on silica gel using ethyl acetate-petrol ether 1:1. This gives 76.2 g of an oil, which is 93% strength after analysis by gas chromatography (yield 38% of theory).

$^1$H-NMR (CDCl$_3$): 1.41 (s, 3H);

(200 MHz, δH in ppm) 1.85 (s, 1H); 2.69 (2 d, 2H, J=18 Hz) 3.52 (2 d, 2H, J=11 Hz) 4.68 (s, 2H); 7.2–7.4 (m, 10H).

Example 3

3-Amino-1-benzylpyrrolidine-2,5-dione

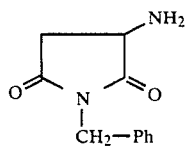

Method A:

56.5 g (0.184 mol) of 95% strength 1-benzyl-3-benzylaminopyrrolidine-2,5-dione are dissolved in 700 ml of ethanol and hydrogenated with 2 g of palladium on charcoal (5%) for 4 hours at 70° C. and 60 bar of hydrogen pressure. The catalyst is then filtered off, the filtrate is concentrated, and the residue is dried at 50° C./0.1 mbar. This gives 36.2 g of product with a content of 94%, determined by gas chromatography and corresponding to a yield of 91% of theory. Melting point 74° to 77° C.

Method B:

1,500 ml of tetrahydrofuran are initially introduced and at 0° C. ammonia is introduced until it condenses in an emplaced dry ice condenser. With continued introduction of ammonia, 374 g (2 mols) of 1-benzyl-$\Delta^3$-pyrroline-2,5-dione are then added dropwise to the mixture as a solution in 500 ml of tetrahydrofuran, and stirring is continued for 3 hours at 0° C. The solution is concentrated in a rotary evaporator, and the residue is taken up in double the amount by weight of ethyl acetate. The crystals obtained after standing for one day at 0° C. are filtered off with suction, and the mother liquor is applied to 2 kg of silica gel. Elution is first carried out with ethyl acetate, then with ethyl acetate/ethanol 1:1. The fractions which only contain the product with an RF value of 0.43 (silica gel, ethyl acetate/ethanol 1:1) are concentrated together. This gives 185.7 g of 3-amino-1-benzylpyrrolidine-2,5-dione, melting point 73° to 75° C.

Example 4

3-Amino-1-benzylpyrrolidine

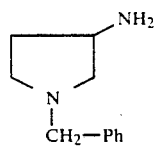

Method A:

34 g (0.9 mol) of lithium aluminum hydride are initially introduced under nitrogen in 500 ml of anhydrous tetrahydrofuran, and 80.8 g (0.4 mol) of 3-amino-1-benzylpyrrolidine-2,5-dione are added dropwise to the mixture as a solution in 400 ml of tetrahydrofuran. The mixture is then refluxed for 20 hours. 34 g of water in 120 ml of tetrahydrofuran, 34 g of 10% strength potassium hydroxide solution and also 136 g of water are added dropwise in succession to the mixture. The solid is filtered off with suction, washed with THF, thoroughly boiled in 250 ml of tetrahydrofuran and again filtered off with suction. The combined filtrates are concentrated in a rotary evaporator, and the residue is distilled under reduced pressure.

Boiling point: 78° to 85° C./0.1 to 0.2 mbar,

Yield: 50.5 g, after analysis by gas chromatography product content of 92% ($\triangleq$66% of theory).

Method B:

Prepared from 1-benzyl-$\Delta^3$-pyrroline-2,5-dione, ammonia and lithium aluminum hydride without isolation of the intermediates.

300 ml of tetrahydrofuran are initially introduced and at 0° C. are introduced until the gas condenses in an emplaced dry ice condenser. With simultaneous introduction of ammonia, a solution of 74.9 g (0.4 mol) of 1-benzyl-$\Delta^3$ -pyrroline-2,5-dione in 100 ml of THF is then added dropwise to the mixture, and stirring is then continued for 3 hours at 0° C. 200 ml of tetrahydrofuran are distilled off from the mixture, and the residue is added dropwise under nitrogen to 34 g (0.9 mol) of lithium aluminum hydride in 700 ml of tetrahydrofuran. The mixture is then refluxed for 10 hours, hydrolysed successively with 34 g of water in 120 ml of tetrahydrofuran, 34 g of 10% strength sodium hydroxide solution and 102 g of water, the precipitate is filtered off with suction and washed with tetrahydrofuran, the filtrate is concentrated in a rotary evaporator, and the residue is distilled. This gives 21 g of a product having a content of 94%, determined by gas chromatography, which corresponds to a yield of 28% of theory.

Method C:

Prepared from 1-benzyl-$\Delta^3$-pyrroline-2,5-dione and benzylamine, followed by catalytic hydrogenation and reduction without isolation of the intermediates.

374 g (2 mols) of 1-benzyl-$\Delta^3$-pyrroline-2,5-dione are dissolved in 2 l of tetrahydrofuran, and 214 g (2 mol) of benzylamine are added to this mixture at 0° to 10° C. Stirring is continued for another hour at room temperature. Hydrogenation is carried out using 30 g of palladium 5% on charcoal at 90° to 100° C. and 100 bar of hydrogen pressure and is completed after 4 hours. The catalyst is filtered off and washed with 100 ml of tetrahydrofuran. 664 g of the resulting solution ($\triangleq$28% of the 2,370 g obtained) are pumped into a solution of 47.6 g (1.25 mols) of lithium aluminum hydride in 700 ml of anhydrous tetrahydrofuran in a 3 l autoclave, and the mixture is then heated at 100° C. for 10 hours. While removing the hydrogen formed, 420 ml of tetrahydrofuran, 48 ml of water in 168 ml of tetrahydrofuran, 48 g of 10% strength potassium hydroxide solution and also 143 ml of water are successively pumped into the mixture, after which the mixture is filtered through a pressure nutsche filter, the filtercake is washed with THF and thoroughly boiled with 500 ml of THF and is again filtered off with suction and the combined filtrates are concentrated. Distillation gives 70.2 g of 3-amino-1-benzylpyrrolidine-2,5-dione having a content of 96.1%, boiling point: 75° to 80° C./0.13 to 0.2 mbar. This corresponds to a yield of 68.4%, based on 1-benzyl-$\Delta^3$-pyrroline-2,5-dione, or to an average yield of 88.1% per reaction step.

Example 5

1-Benzyl-3-benzylaminopyrrolidine

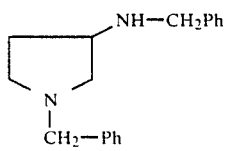

Method A:

1,000 g (5.34 mols) of 1-benzyl-Δ³-pyrroline-2,5-dione are dissolved in 2.5 l of tetrahydrofuran, and 572 g (5.34 mols) of benzylamine are added with stirring at 10° to 20° C. The mixture is left to stand for 24 hours at room temperature, after which 360 g are removed from the resulting solution (3,848 g of total weight) and added to a solution of 38 g (1 mol) of lithium aluminum hydride in 380 ml of absolute dehydrated tetrahydrofuran. The mixture is refluxed for 20 hours, 500 ml of tetrahydrofuran, 38 g of water and 120 ml of tetrahydrofuran, 38 g of 10% strength potassium hydroxide solution and 114 g of water are then sucessively added to the mixture. The salts are filtered off with suction, washed with tetrahydrofuran, the filtrate is concentrated, and the residue is distilled.

Boiling point: 151° to 164° C./0.19 mbar, yield: 111.3 g, content after analysis by gas chromatography 99.6%, corresponding to a yield of 84% of theory, based on 1-benzyl-Δ³-pyrroline-2,5-dione.

Method B:

450 g of the solution obtained by method A from benzylamine and 1-benzyl-Δ³-pyrroline-2,5-dione are reduced with 47.6 g (1.25 mol) of lithium aluminum hydride in an autoclave over a period of 10 hours at 100° C. The work up is carried out as in method A of Example 4. This gives 144.1 g (86% of theory) of 1-benzyl-3-benzylaminopyrrolidine.

Method C:

56.7 g (0.4 mol) of boron trifluoride-diethyl ether adduct are added dropwise under nitrogen to a solution of 28.3 g (0.75 mol) of sodium borohydride in 700 ml of diethylene glycol dimethyl ether. At 0° to 5° C., 216 g (0.3 mol) of the solution of 1-benzyl-3-benzylaminopyrrolidine-2,5-dione in tetrahydrofuran obtained by method A are added dropwise to this mixture. Stirring is continued for 15 hours at 100° C. 223 ml of 6N hydrochloric acid are then added dropwise, and the mixture is heated to 100° C. until the evolution of gas is complete. After cooling, the mixture is further diluted with water, and the pH is brought to 11 using sodium hydroxide solution. The resulting oil is taken up in toluene, the toluene layer is dried with sodium sulphate, and the solvent is removed at a bath temperature of 80° C./5 mbar. The high vacuum distillation gives 60.7 g of product, boiling point 165°–170° C./0.21 mbar, having a content of 97.6% which corresponds to a yield of 74% of theory.

Example 6

1-Benzyl-3-benzylamino-3-methylpyrrolidine

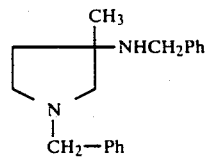

51 g of 93% pure 1-benzyl-3-benzylamino-3-methylpyrrolidine-2,5-dione (0.154 mol) are reduced in 330 ml of dimethoxyethane using 12.4 g (0.33 mol) of lithium aluminum hydride. The work up is carried out as in A of Example 5.

Boiling point: 141° to 143° C./0.13 mbar. Yield: 30.1 g, content 98.5% after analysis by gas chromatography ($\triangleq$69% of theory).

Example 7

3-Amino-1-benzylpyrrolidine

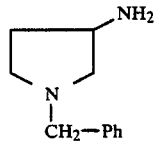

4,151 g (22.2 mols) of 1-benzyl-Δ³-pyrroline-2,5-dione are initially introduced in 10.4 l of tetrahydrofuran (water content <0.1%), and 2,375 g (22.2 mols) of benzylamine are added dropwise to the solution at 10°–30° C. Stirring is continued overnight at room temperature, the mixture is then diluted with 10 l of tetrahydrofuran (water content <0.1%) and hydrogenated at 90°–100° C. and 90–100 bar over 300 g of 5% palladium on charcoal. To complete the debenzylation, 100 g of catalyst are again added to the mixture towards the end of the hydrogen absorption, and the hydrogenation is continued under the conditions described above. The catalyst is then filtered off and washed with 1.5 l of tetrahydrofuran (water content <0.1%).

The filtrate (except for a sample of 270 g≈0.26 mol) and also 7 l of tetrahydrofuran (water content <0.1%) are pumped at 20° C. into 18.5 kg (48.7 mols) of initially introduced 10% strength (lithium aluminum hydride solution in tetrahydrofuran in a 130 l stirred autoclave, and the line is flushed with 2 l of tetrahydrofuran (water content <0.1%). The mixture is then heated for 10 hours at 100° C., the hydrogen pressure is released, and 16.8 l of tetrahydrofuran, 1,850 ml of water in 5.5 l of tetrahydrofuran, 1,850 ml of 10% strength potassium hydroxide solution and also 5.5 l of water are pumped into the mixture at 20°–30° C. The mixture is stirred until a constant pressure is obtained, the hydrogen pressure is released, and the reaction mixture is filtered. The filtercake is thoroughly boiled with tetrahydrofuran, is filtered again, and the combined filtrates are concentrated in a rotary evaporator. The residue (3,840 g) is distilled in a high vacuum without a column and without fractionation to give 3,336 g of crude distillate which is distilled over a 60 cm Vigreux column to give 3,131 g of product (boiling point 94°–96° C./0.18 mbar) having a content of 96.7%, determined by gas chromatography. This corresponds to a yield of 78.3%, based on 1-benzyl-Δ³-pyrroline-2,5-dione, or an average yield of 92.2% per reaction step.

It will be appreciated that the instant specification and claims are set forth by way of illustration and not limitation, and that various modifications and changes may be made without departing from the spirit and scope of the present invention.

What is claimed is:

1. A process for preparing a 3-amino-1-benzylpyrrolidine of the formula

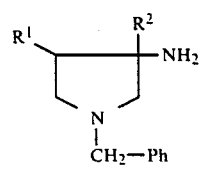

(I)

in which $R^1$ and $R^2$ each independently is H or $C_1-C_6$ alkyl, and

Ph is phenyl, comprising reacting a 1-benzyl-$\Delta^3$-pyrroline-2,5-dione of the formula

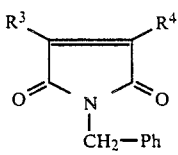

in which $R^3$ and $R^4$ each independently is H or $C_1-C_6$ alkyl, with a nitrogen nucleophile of the formula $$R^5NH_2 \quad (III)$$

in which $R^5$ is benzyl, naphthylmethyl or phenyl-$CHR^6$, and $R^6$ is $C_1-C_6$-alkyl or phenyl, at about $-40°$ to $200°$ C. to give a 3-amino-1-benzylpyrrolidine 2,5-dione of the formula

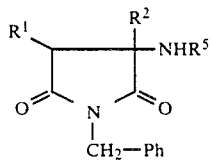

and $R^5$ is subsequently cleaved off to give a 3-amino-1-benzylpyrrolidine-2,5-dione of the formula

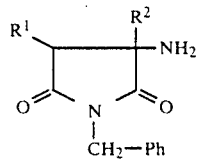

and completely reducing the carbonyl groups to form the 3-amino-1-benzylpyrrolidine of the formula (I).

2. A process for preparing a compound of the formula

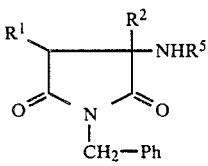

in which $R^1$ and $R^2$ each independently is H or $C_1-C_6$-alkyl,
$R^5$ is benzyl, naphthylmethyl or phenyl-$CHR^6$, and
$R^6$ is $C_1-C_6$-alkyl or phenyl, comprising reducing a compound of the formula

by catalytic hydrogenation or by reaction with a hydride or mixed hydride of the 3rd main group of the periodic table of the elements.

3. A process according to claim 2, wherein the reducing agent used is boron hydride, sodium bis-(2-methoxy)-aluminum hydride, lithium aluminum hydride or sodium borohydride.

4. A process according to claim 3, wherein a Lewis acid is also present.

5. A process according to claim 2, wherein the reduction is carried out in an ether or alkylaromatic or mixture thereof.

6. A process according to claim 1, wherein $R^1$ to $R^4$ denote hydrogen.

7. A process according to claim 1, wherein the reaction sequence is carried out without isolation of the intermediates.

8. A process for preparing 3-amino-1-benzylpyrrolidine according to claim 1, comprising reacting 1-benzyl-$\Delta^3$-pyrroline-2,5-dione with benzylamine, debenzylating the product by catalytic hydrogenation selectively to give 3-amino-1-benzylpyrrolidine-2,5-dione, and reducing the 3-amino-1-benzylpyrrolidine-2,5-dione with lithium aluminum hydride or sodium borohydride/Lewis acid.

9. A process according to claim 8, wherein the reaction sequence is carried out in a cyclic or open-chain ether without isolation of the intermediates, and palladium on charcoal is used as the hydrogenation catalyst.

10. A process for preparing 1-benzyl-3-benzylaminopyrrolidine, comprising reacting 1-benzyl-$\Delta^3$-pyrrolidine-2,5-dione with benzylamine at about $-40°$ to $200°$ C. to give 1-benzyl-3-benzylaminopyrrolidine-2,5-dione, and reducing the 1-benzyl-3-benzyl amino pyrrolidine-2,5-dione with lithium aluminum hydride or sodium borohydride/Lewis acid.

11. A process according to claim 10, wherein the reaction sequence is carried in a cyclic or open-chain ether without isolation of the intermediate.

* * * * *